United States Patent
Iddan

(10) Patent No.: US 7,460,896 B2
(45) Date of Patent: Dec. 2, 2008

(54) IN VIVO DEVICE AND METHOD FOR COLLECTING OXIMETRY DATA

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 272 days.

(21) Appl. No.: 10/901,177

(22) Filed: Jul. 29, 2004

(65) Prior Publication Data

US 2005/0027178 A1 Feb. 3, 2005

Related U.S. Application Data

(60) Provisional application No. 60/490,481, filed on Jul. 29, 2003.

(51) Int. Cl.
*A61B 5/1455* (2006.01)
(52) U.S. Cl. ...................................... 600/339
(58) Field of Classification Search ................. 600/322, 600/323, 339, 340, 342, 343
See application file for complete search history.

(56) References Cited

U.S. PATENT DOCUMENTS

| | | | |
|---|---|---|---|
| 4,278,077 A | | 7/1981 | Mizumoto |
| 4,791,935 A | * | 12/1988 | Baudino et al. ............. 600/333 |
| 4,803,992 A | * | 2/1989 | Lemelson .................. 600/342 |
| 5,329,922 A | * | 7/1994 | Atlee, III .................. 600/328 |
| 5,357,954 A | * | 10/1994 | Shigezawa et al. .......... 600/339 |
| 5,438,987 A | * | 8/1995 | Thacker et al. ............. 600/337 |
| 5,604,531 A | | 2/1997 | Iddan et al. |
| 5,762,770 A | | 6/1998 | Pritchard et al. |
| 5,833,603 A | | 11/1998 | Kovacs et al. |
| 5,853,005 A | | 12/1998 | Scanlon |
| 5,892,144 A | | 4/1999 | Meller et al. |
| 5,932,480 A | | 8/1999 | Maruo et al. |
| 6,074,349 A | | 6/2000 | Crowley |
| 6,125,291 A | * | 9/2000 | Miesel et al. .............. 600/333 |
| 6,165,128 A | | 12/2000 | Cespedes et al. |
| 6,240,312 B1 | | 5/2001 | Alfano et al. |
| 6,304,766 B1 | * | 10/2001 | Colvin, Jr. ................ 600/317 |
| 6,584,348 B2 | | 6/2003 | Glukhovsky |
| 6,607,301 B1 | | 8/2003 | Glukhovsky et al. |
| 6,632,175 B1 | * | 10/2003 | Marshall ................... 600/309 |

(Continued)

FOREIGN PATENT DOCUMENTS

| WO | WO 01/07919 | 2/2001 |
|---|---|---|

(Continued)

OTHER PUBLICATIONS

Wang, et al., "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.

(Continued)

*Primary Examiner*—Eric F Winakur
(74) *Attorney, Agent, or Firm*—Pearl Cohen Zedek Latzer, LLP

(57) ABSTRACT

An in vivo device and a method for collecting and measuring oximetry data in a body lumen, such as using a swallowable capsule. The in vivo device may include instruments for collecting oximetry data, for example an illuminator and an oximetry data detector.

18 Claims, 4 Drawing Sheets

U.S. PATENT DOCUMENTS

| | | |
|---|---|---|
| 6,950,690 B1 * | 9/2005 | Meron et al. .......... 600/424 |
| 2001/0031502 A1 | 10/2001 | Watson et al. |
| 2001/0053535 A1 | 12/2001 | Bashir et al. |
| 2002/0111544 A1 | 8/2002 | Iddan |
| 2002/0146368 A1 | 10/2002 | Meron et al. |
| 2002/0198470 A1 * | 12/2002 | Imran et al. .......... 600/587 |
| 2003/0040685 A1 | 2/2003 | Lewkowicz et al. |
| 2003/0195415 A1 | 10/2003 | Iddan |

FOREIGN PATENT DOCUMENTS

| | | |
|---|---|---|
| WO | WO 01/50941 | 7/2001 |
| WO | WO 01/65995 A2 | 9/2001 |
| WO | WO 02/054932 | 7/2002 |
| WO | WO03/094723 | 11/2003 |
| WO | PCT/IL03/01080 | 12/2003 |
| WO | WO2004/004540 | 1/2004 |
| WO | WO 2004/014227 | 2/2004 |
| WO | WO 2004/039233 | 5/2004 |
| WO | WO 2004/045395 | 6/2004 |

OTHER PUBLICATIONS

Roubik, et al., "Reference Microelectrodes Design Evaluation for On-Chip ISFET-Based Microsensors for "in vivo" Blood Measurements".

F. Vald's-Perezgasga, et al., "Isfet Applications in Biological Matter: An Overview", downloaded Oct. 27, 2002, www.cinstrum.unam.mx/revista/pdfv4n3/art3.PDF.

"The Basics: How PRO2 works", downloaded May 6, 2003, http://www.imagyn.com/criticalcare/pulse_reflectance_oximetry_pg1.htm.

"UCLA completes first 14 cases with Imagyn's reflectance pulse oximetry system", downloaded May 6, 2003, http://www.imagyn.com/press_releases/01_28_02_RPO_14_Cases.htm.

* cited by examiner

IN VIVO DEVICE AND METHOD FOR COLLECTING OXIMETRY DATA

CROSS REFERENCE TO RELATED APPLICATIONS

This application claims the benefit of U.S. Provisional Application No. 60/490,481, filed on Jul. 29, 2003.

FIELD OF THE INVENTION

The present invention relates to the field of oximetry, and particularly to an in vivo device including instruments for collecting oximetry data.

BACKGROUND

Measuring the oxygenation of hemoglobin in the blood stream (oximetry) is typically performed by instruments that may direct light, such as for example red and/or infrared light, into a tissue or organ, such as for example into the flesh of a finger, and detect the signals produced by the varying rates of diffusion of such light from such tissue or organ.

Various circulatory diseases may affect the oxygenation of hemoglobin in the blood stream. Furthermore numerous diseases of localized areas of the body may produce specific oximetric readings in the local area of such disease. Gastrointestinal diseases such as for example ulcerative colitis, eschemia, Crohn's Disease, gastric tumors and others may produce specific oximetric readings in the areas of the gastrointestinal tract where such diseases are manifest. It may therefore be possible to use oximetric readings as a diagnostic tool to detect and locate specific conditions in for example the gastrointestinal ("GI") tract or in other locations in the body.

There is therefore a need for a device, system and method for collecting oximetry readings from within lumens or cavities or in other locations within the body.

SUMMARY OF THE INVENTION

Methods and devices according to embodiments of the invention are used, inter alia, to collect oximetry data in a body lumen. Embodiments of the invention relate to a typically non-invasive autonomous ingestible device, which enables in situ the measurement of, for example, oxygenation of hemoglobin in a blood stream.

The device, according to one embodiment, may include instruments or components for collecting oximetry data. According to some embodiment instruments for collecting oximetry data may include, for example, an illuminator and a detector. According to some embodiment instruments for collecting oximetry data may include, for example a reflectance oximeter or other oximeter devices as are known in the art.

A method for collecting oximetry data in an in vivo device, according to an embodiment of the invention, includes the step of introducing into a body lumen or a body cavity an in vivo device. According to one embodiment an in vivo device may illuminate areas of a body lumen with a light source. According to some embodiment filters may filter certain wavelengths of light to detect sidescatter light that may be reaching a detector. Thus a detection, of diffused light as was diffused in and from a tissue, by a detector may enable the collection and measurement of oxygenated hemoglobin in the blood passing through such tissue. Other oximetry detection techniques may be used.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
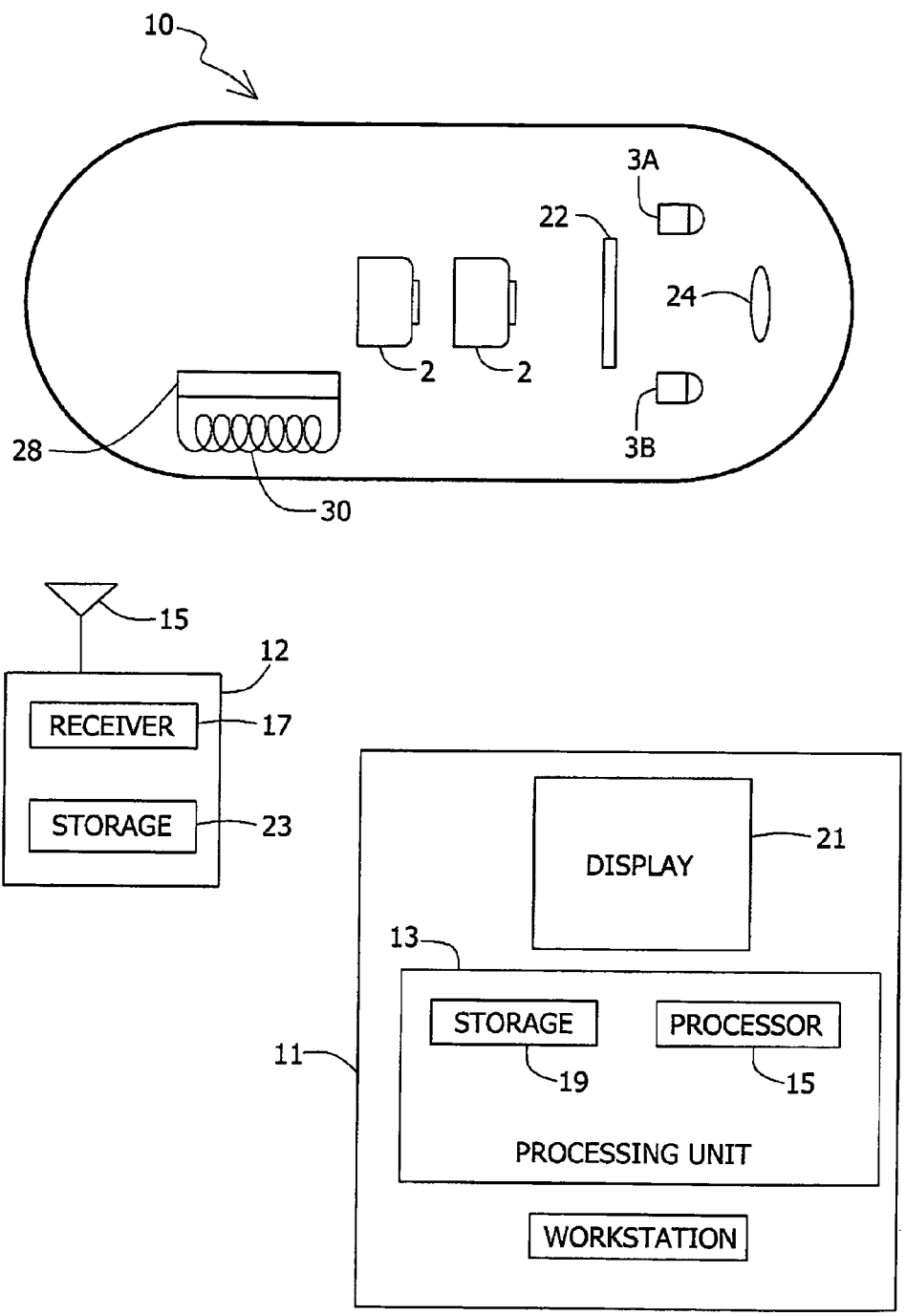
FIG. 1 is a block diagram schematically illustrating a system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various embodiments of the invention will be described. For purposes of explanation, specific examples are set forth in order to provide a thorough understanding of at least one embodiment of the invention. However, it will also be apparent to one skilled in the art that other embodiments of the invention are not limited to the examples described herein. Furthermore, well-known features may be omitted or simplified in order not to obscure embodiments of the invention described herein.

Reference is now made to FIG. 1, which is a schematic illustration of an exemplary system with an in vivo device 10 for collecting oximetry data, and a data receiver and/or recorder 12 and a workstation 11. A data receiver and/or recorder 12 may take other suitable configurations. The data receiver and/or recorder 12 may transfer the received information to another computing device, such as a workstation 11 or personal computer, where the data may be further analyzed, stored, and/or displayed to a user.

Device 10 typically may be or may include an autonomous swallowable capsule, but device 10 may have other shapes and need not be swallowable or autonomous. Embodiments of device 10 are typically autonomous, and are typically self-contained. For example, device 10 may be a capsule or other unit where all the components are substantially contained within a container or shell, and where device 10 does not require any wires or cables to, for example, receive power or transmit information. Device 10 may communicate with data receiver and/or recorder 12 and a workstation 11 to provide display of data, control, or other functions. For example, power may be provided by an internal battery or a wireless receiving system. Other embodiments may have other configurations and capabilities. For example, components may be distributed over multiple sites or units. Control information may be received from an external source. In one embodiment, all of the components may be sealed within the device body (the body or shell may include more than one piece); for example, an imager 22, illumination units 3A and 3B, power units 2, transmitter 28, antenna, and control unit, may all be sealed within the device body.

According to one embodiment the workstation 11 includes a controller or processor 15, a storage unit 19 and display 21. In other embodiments, each of the various components need not be required; for example, an internal device may transmit or otherwise transfer (e.g., by wire, via radio waves) information directly to a display or processing system 21.

Figure 2:
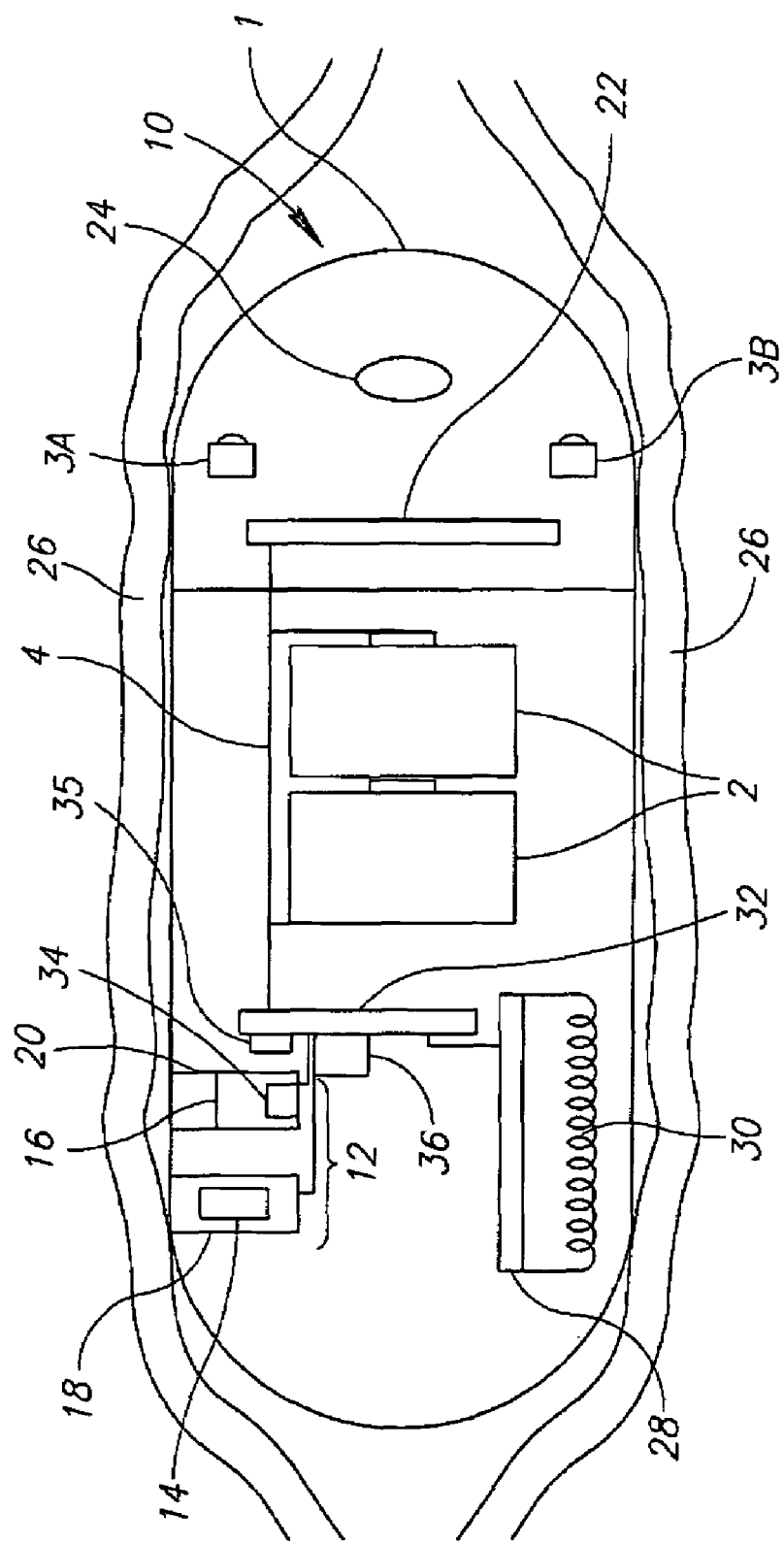
FIG. 2 is a schematic diagram of an in vivo device including instruments capable of collecting oximetry readings, in accordance with an embodiment of the invention.

Reference is made to FIG. 2, a schematic diagram of an in vivo device 10 capable of collecting oximetry information, in accordance with an embodiment of the invention. According to one embodiment, in vivo device 10 may be or may include an autonomous swallowable capsule, but device 10 may have other shapes and need not be swallowable or autonomous. According to some embodiments, in vivo device 10 may be introduced into the gastro-intestinal or other tract, lumen or cavity of a body. In vivo device 10 may in some embodiments collect, in addition to oximetry information, data, images or other information as it passes through the GI tract. In other embodiments, in vivo device 10 may be introduced into other lumens, such as for example, the circulatory, respiratory or urogenital tracts where it may sense, collect or transmit data. In vivo device 10 may include shapes and forms other than a capsule.

According to one embodiment, in vivo device 10 may be round, oval or shaped in such other manner as may be appropriate for the body lumen or cavity into which it is introduced or through which it passes. In vivo device 10 may be fashioned in shapes or forms other than a capsule. According to some embodiments, in vivo device 10 may include an optical dome 1, image sensor 22, one or more optical components such as a lens 24, a power source, such as for example, batteries 2, one or more illumination devices 3A and 3B to illuminate in vivo sites and a series of connections or wires 4 between various components of in vivo device 10. Other components and functions may be added to in vivo device 10. In vivo device 10 according to an embodiment of the invention may be similar to embodiments described in International Application WO 01/65995 entitled A DEVICE AND SYSTEM FOR IN-VIVO IMAGING and/or in U.S. Pat. No. 5,604,531 entitled IN-VIVO VIDEO CAMERA SYSTEM, each of which are assigned to the common assignee of the present invention and each of which are hereby incorporated by reference. Furthermore, a receiving and/or display system suitable for use with embodiments of the invention may also be similar to embodiments described in WO 01/65995 and/or in U.S. Pat. No. 5,604,531.

According to one embodiment, in vivo device 10 may include or be fitted with units or instruments for collecting oximetry data 12 that may be situated on or adjacent to an external surface of in vivo device 10. In other embodiments instruments for collecting oximetry data 12 may be located elsewhere on in vivo device 10. In some embodiments instruments for collecting oximetry data 12 may be constructed in two or more segments, such as an illuminator 14 and an oximetry data detector 16. Oximetry data detector 16 may be sensor device(s), for example, optical sensing devices such as photodiodes, imagers or any other suitable imaging devices.

In some embodiments, instruments for collecting oximetry data 12 may include a reflectance oximeter or other oximeter devices as are known in the art. According to one embodiment, illuminator 14 may be recessed into an illuminator cavity 18, and oximetry data detector 16 may be recessed into a detector cavity 20. Recessing illuminator 14 into illuminator cavity 18 may minimize backscatter and sidescatter light, as described below. A cavity such as cavity 18 or 20 may be, for example, a recessed area formed by the shell of the device 10, or for example may be a separate unit formed and connected to device 10, or may take other suitable configurations. The cavities 18 or 20 may allow limited line of sight access in a narrowed angle for light sources or detectors to a body lumen, while minimizing backscatter or sidescatter. Recessing oximetry data detector 16 into detector cavity 20 may likewise reduce or minimize sidescatter light that is detected by oximetry data detector 16. In a typical embodiment, the illuminating element of illuminator 14 may be recessed from the external walls of the capsule. In some embodiments, illuminator 14 may be constructed into the side of in vivo device 10 without an illuminator cavity 18. In some embodiments, oximetry data detector 16 may be constructed into the side of device 10 without a detector cavity 20. Typically, oximetry data detector 16 is configured so that as the device 10 moves, generally the same region is detected via illuminator 16. According to some embodiments a plurality of detectors may be arranged in a line along the expected direction of movement of the device.

In some embodiments, illuminator 14 may include two or more illumination elements, each of which may illuminate using different wavelengths of the light spectrum, such as for example red, infrared light or other suitable wavelengths. Illuminator 14 may be a light emitting diode (LED), a laser or another type of illumination device capable of creating flashes of light or other electromagnetic radiation that are suitable for detection by oximetry data detector 16 and for measuring oxygenation of hemoglobin in blood, embodiments of such lights are known in the art. Red and infrared light with frequencies of approximately 650-660 nm and 850-910 nm are frequently used for measuring the oxygenation of hemoglobin in the blood, though other parts of the light or electromagnetic spectrum may also be suitable. Pulses of light suitable for measuring the oxygenation of hemoglobin in blood in accordance with an embodiment of the invention may typically be from a fraction of a second to one or two seconds long. Other pulse lengths may be possible. In a typical embodiment, light pulses may be minimized to the extent possible in order to preserve power consumed by in vivo device 10. Illuminator 14 may in some embodiments be attached by wire or other connection to a power source such as battery 2, within in vivo device 10. In some embodiments, illuminator 14 and/or oximetry data detector 16 may be controlled through a controller 35.

In some embodiments, in vivo device 10 may include a transmitter, such as a transmitter 28 (typically a wireless transmitter), and an antenna 30, for transmitting data to an external receiving unit 12 (for example, as was described with reference to FIG. 1). Transmitter 28 may include control capability for, for example controlling the various operations of device 10, although control capability or one or more aspects of control may be included in a separate component. Transmitter 28 is typically an ASIC (application specific integrated circuit), but may be of other constructions; for example, transmitter 28 may be a processor executing instructions. Device 10 may include a processing unit separate from transmitter 28 that may, for example, contain or process instructions. According to some embodiments, the transmitter 28 is a wireless transmitter which may utilize an antenna 30. Such a receiving unit may be similar to embodiments described in U.S. Pat. No. 5,604,531, and/or application WO 01/65995, each incorporated by reference herein in their entirety. According to one embodiment, transmitter 28 may include processing and/or controlling capabilities or may be associated with a separate processor or with controller 35. For example, transmitter 28 or a separate processor may control illuminator 14 and/or oximetry data detector 16. According to one embodiment, transmitter 28 or a separate processor may include, for example, an ASIC (application specific integrated circuit) or other circuit 32 that may be operably in communication with a component in the in-vivo device for example: connected to any of illuminator 14 and/or oximetry data detector 16 and/or and/or transmitter 28 and/or controller 35. According to one embodiment, transmitter 28 may include transmitting capabilities, for example, operating on a minimum shift keying (MSK) modulation system to effect transmitting of digital signals on radio frequencies to a receiving system. In alternate embodiments, other signals and other electronic and processing components may be used.

According to some embodiments, in operation, in vivo device 10 may be introduced into a body, such as for example into a GI tract by, for example, swallowing. Upon such introduction or upon some other event as may in some embodiments be predefined or preprogrammed into in vivo device 10, illuminator 14 may illuminate a tissue 26 or other segment of a wall of a body lumen or other body part that may be adjacent at such time to instruments for collecting oximetry data 12. Light, or other electromagnetic radiation, that is directed and diffused into such tissue 26 may be detected by oximetry data detector 16. A processor 34 that may be operably linked to oximetry data detector 16 may collect and/or calculate oximetric readings based on the detection by oximetry data detector 16 of diffused light or other electromagnetic radiation from tissue 26. Such calculations may in some embodiments be performed remotely from in vivo device 10, for example in an external receiving unit, external workstation, etc. Processor 34 may convey signals or oximetry readings to circuit 32. In some embodiments, some or all of processor 34, circuit 32, transmitter 28 and controller 35 may be included in a single structure. Circuit 32 may convey signals or oximetry readings to transmitter 28, which by way of antenna 30 may broadcast such signals or readings to an external receiving unit. Such signals may be broadcast together with or separately from image or other data that may in some embodiments be collected by in vivo device 10. In some embodiments, signals or readings may be stored in an optional memory 36.

Instruments for collecting oximetry data 12 may illuminate a tissue 26 by way of illuminator 14, and may collect readings on the oxygenation of hemoglobin in blood by way of oximetry data detector 16 at regular, continuous, periodic or predetermined intervals as it moves through a body lumen or body cavity such that readings on the oxygenation of hemoglobin in blood may be collected from various areas of such lumen or cavity.

Figure 3:
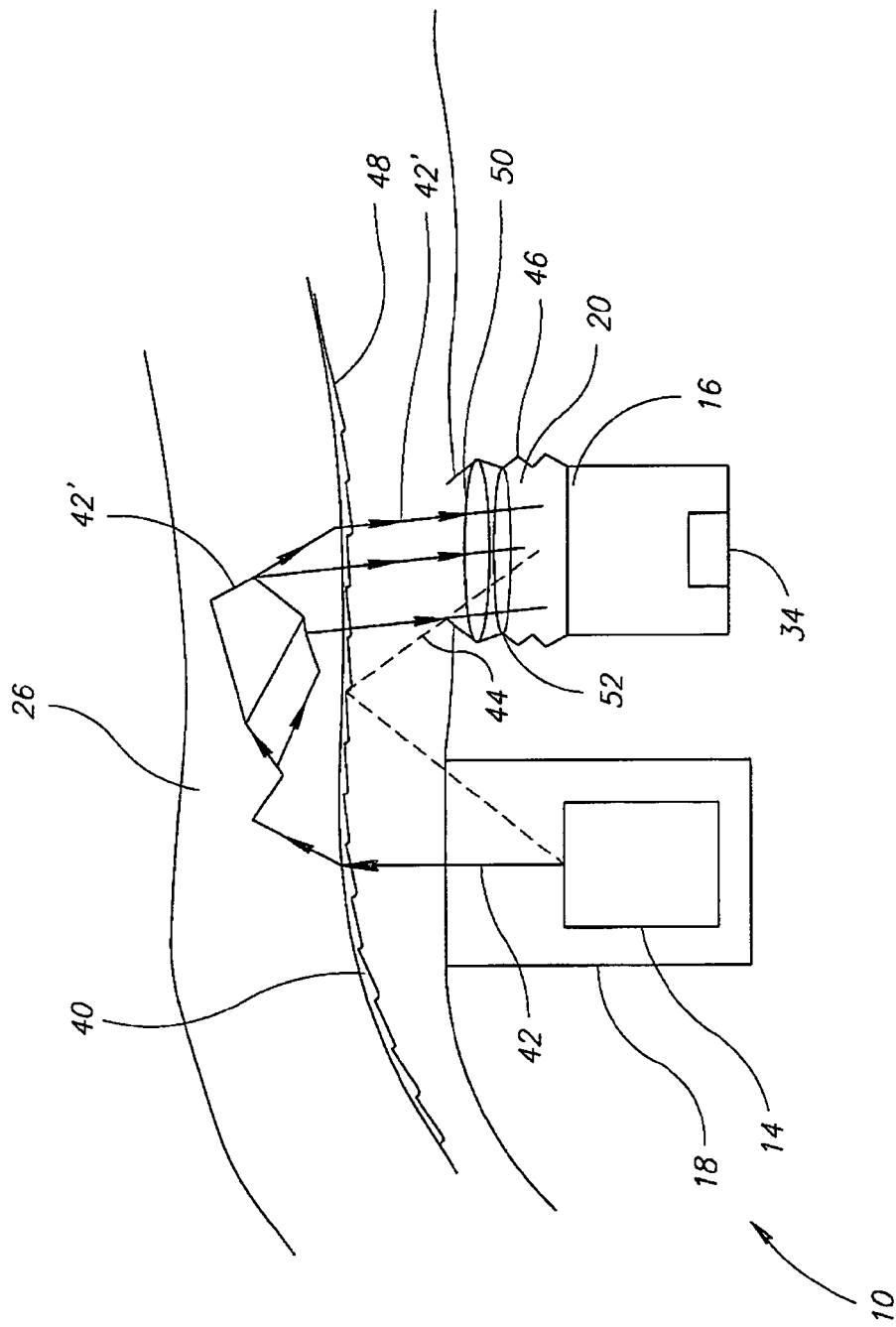
FIG. 3 is a schematic diagram of the reflection and diffusion of light directed into a tissue and detected by an instrument capable of collecting oximetry readings in accordance with an embodiment of the invention.

Reference is made to FIG. 3, a schematic diagram of the reflection and diffusion of light directed into a tissue and detected by instruments for collecting oximetry data 12 in accordance with an embodiment of the invention. In some embodiments, it may be preferable that all or substantially all of the red or infrared light that reaches oximetry data detector 16 or is detected by oximetry data detector 16, is light that has been diffused through tissue 26, such that it has been diffused and reflected back by blood in such tissue 26. In FIG. 3, red, infrared or other wavelengths of electromagnetic radiation such as for example light 42 (shown as a single line with an arrow) are directed by illuminator 14 to tissue 26. Preferably, all or substantially all of such light 42 is absorbed or diffused into tissue 26. Detector 26 may detect diffused light 42' (shown as a pluralaty of lines with arrows) in tissue 26 and readings of the oxygenation of hemoglobin in blood may be calculated based on the absorption of such diffused light 42' in the blood of tissue 26. Such calculation may be performed by processor 34 or by another component, which in some embodiments may be inside, and in other embodiments may be external to in vivo device 10. In some embodiments, and with respect to some tissues 26 in body lumens or body cavities, some of light 42 may be reflected off of the outside layer 40 of tissue 26, instead of being diffused into tissue 26. Such outside layer 40 of tissue 26, may in certain body lumens or cavities be moist or coated with a layer of for example, water, mucus or other fluids 48, and such fluids 48 may increase the amount of light 42 that is reflected off of, rather than diffused into tissue 26. Scattered rays of such reflected light, which may be referred to as sidescatter 44 (shown as dashed lines), may be detected by oximetry data detector 16 and, may unless otherwise accounted for or avoided, skew or invalidate readings of the oxygenation of hemoglobin in blood as are collected or calculated by oximetry data detector 16.

Various suitable methods of reducing or eliminating sidescatter 44 and its effects on readings of the oxygenation of hemoglobin in blood may be used. In one embodiment, an uneven or non-reflective surface 46 may be included in, for example, the upper portions of detector cavity 20. Such non-reflective surface may in some embodiments be coated with a suitable coating, for example, a Black High Emissivity Coating to absorb sidescatter 44. Other coatings or surface patterns may be used. In some embodiments, illuminator 14 may emit collimated light that may result in less sidescatter light. In some embodiments, one or both of illuminator cavity 18 and/or detector cavity 20 may be angled such that for example, oximetry data detector 16 is pointed towards an area of a body lumen or body cavity that is to be illuminated, but away from the light 42 emitted by illuminator 14 and away from the direction at which sidescatter 44 may be reflected.

In some embodiments, sidescatter 44 that may be included in the calculation of the oxygenation of hemoglobin in blood, may be minimized by modulating light 42 at two or more wavelengths. Such two or more wavelengths may preferably be refracted similarly, or to similar extents, by fluid 48, but may be refracted or diffused differently, or to different extents, by tissue 26. (Diffusion in some embodiments may be measured by for example, the Boltzman Photo Diffusion Equation, though other suitable measurements or equations are possible.) For example, illuminator 14 may direct a beam of light 42 at 650 Nm and a beam of light 42 at 600 Nm. (As described herein, more than one illuminator 14 may be used.) Each of such two beams may be refracted or reflected to the same extent by fluid 48, but may be subject to different diffusion ratios in tissue 26. For example, light 42 at 600 nm may be diffused by tissue 26 to a greater extent than light 42 at 650 nm. One or more filter(s) may be added to detector cavity 20, such that one of such filters 50, may for example filter light with a wavelength of 650 nm, and a second of such filters 52, may filter light 42 with a wavelength of 600 nm. By evaluating the difference between the light 42 at 650 nm filtered by a filter 50 and the light 42 at 600 nm filtered by filter 52, a determination may be made as to how much of light 42 at 660 nm has reached oximetry data detector 16 after being diffused in tissue 26, and how much has reached oximetry data detector 16 as sidescatter 44. In some embodiments, readings of the oxygenation of hemoglobin in blood may be disregarded or adjusted if sidescatter 44 reaching oximetry data detector 16 exceeds a threshold amount that may make such readings unreliable. Other wavelengths and number of wavelengths may be used.

Figure 4:
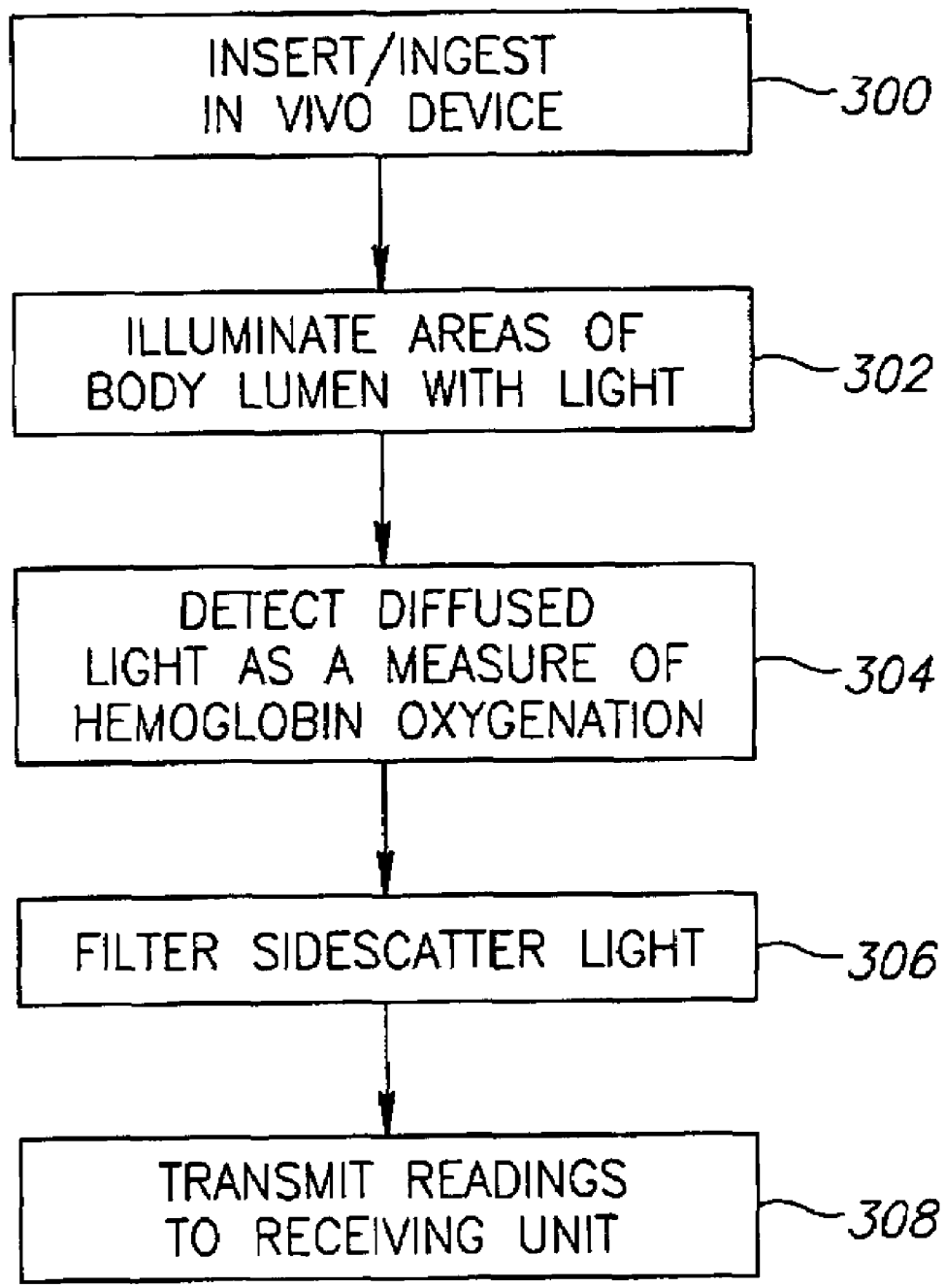
FIG. 4 is a flow diagram depicting a method for collecting oximetry readings using an in vivo device, in accordance with an embodiment of the invention.

Reference is made to FIG. 4, a flow diagram depicting a method of in vivo measuring of oximetry, in accordance with an embodiment of the invention. In operation 300 an in vivo device may be ingested or otherwise introduced into a body lumen or body cavity. For example, a device such as an autonomous device may be used; other suitable devices may be used. In operation 302, an in vivo device may illuminate areas of a body lumen with light 42 such as red, infrared or other suitable wavelengths and/or electromagnetic radiation In operation 304, a detector may detect diffused light as was diffused in and emerged from a tissue, and may collect measurements of oxygenated hemoglobin in the blood passing through such tissue. Such light may be diffused into tissue of a body lumen. In some embodiments, in operation 306, filters may filter certain wavelengths of light to detect sidescatter light that may be reaching detector. In some embodiments, in operation 308, readings of the oxygenation of hemoglobin in blood may be transmitted by an in vivo device to a receiving unit In some embodiments such data may be transferred along with other data, such as for example image data, collected by an in vivo device. Other operations or series of operations may be used.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An autonomous in-vivo device comprising a unit to measure oxygenation of hemoglobin in a blood stream, said device when inside a body not including any physical connection to an additional device, the unit comprising:
   at least two cavities limiting backscatter or sidescatter light access, wherein a first of said at least two cavities includes either an illumination source or a detector recessed therein and a second of said at least two cavities includes the other of said illumination source or said detector recessed therein,
   said unit arranged such that light emitted by the illumination source is detectable by the detector when said device is inside a body.

2. The device according to claim 1, comprising a filter to filter sidescatter light.

3. The device according to claim 1, comprising an oximetry data detector.

4. The device according to claim 1, further comprising an optical dome behind which are situated an imager, an optical element and an illumination device to illuminate in vivo sites.

5. The device according to claim 1,. comprising a wireless transmitter.

6. The device according to claim 1, comprising an instrument to collect oximetry data.

7. The device according to claim 1, wherein said cavity is recessed into one side of the device.

8. The device according to claim 1, wherein the illuminator and detector are arranged for obtaining reflectance measurements.

9. The device according to claim 1, wherein said at least one cavity comprises a non-reflective surface to absorb backscatter or sidescatter light.

10. The device according to claim 1, wherein said in-vivo device is a capsule.

11. A system for measuring the oxygenation of hemoglobin in a blood stream, the system comprising:
    an autonomous in vivo device that, when inside a body does not include any physical connection to an additional device, comprising
    an instrument to collect oximetry data;
    at least two cavities limiting backscatter or sidescatter light access, wherein a first of said at least two cavities includes either an illumination source or a detector recessed therein and a second of said at least two cavities includes the other of said illumination source or said detector recessed therein,
    said unit arranged such that light emitted by the illumination source is detectable by the detector when said device is inside a body; and
    an external receiving unit to receive transmitted information.

12. The system according to claim 11, wherein the receiving unit includes at least a component selected from the group consisting of: a recorder unit, a storage unit and a workstation.

13. The system according to claim 11, comprising a controller to calculate oximetric readings from diffused light received by the in-vivo device.

14. A method of in vivo measuring of oximetry, the method comprising:
    inserting an autonomous in vivo device into a body lumen, said device when inside the body lumen not including any physical connection to an additional device;
    illuminating tissue of said body lumen with an illuminator in the device, the illuminator recessed in a cavity limiting backscatter or sidescatter light access;
    detecting light diffused from a tissue of said body lumen by a detector in the device, the detector recessed in a cavity limiting backscatter or sidescatter light access; and
    calculating oximetric readings based on the detected diffused light.

15. The method according to claim 14, comprising illuminating areas of the body lumen using different wavelengths of the light spectrum.

16. The method according to claim 14, comprising filtering sidescatter light.

17. The method according to claim 14, comprising transmitting said measurements to a receiving unit.

18. The method according to claim 14, comprising collecting and transmitting imaging information.

* * * * *